(12) United States Patent
Paul et al.

(10) Patent No.: US 7,768,261 B2
(45) Date of Patent: Aug. 3, 2010

(54) APPARATUS AND METHOD FOR IMAGE ALIGNMENT FOR COMBINED POSITRON EMISSION TOMOGRAPHY (PET) AND MAGNETIC RESONANCE IMAGING (MRI) SCANNER

(75) Inventors: Rainer Paul, Kapsweyer (DE); Matthias J. Schmand, Lenoir City, TN (US); Charles H. Hayden, Jr., Knoxville, TN (US); James Corbeil, Knoxville, TN (US); Christian J. Michel, Lenoir City, TN (US); Ziad Burbar, Knoxville, TN (US); Volker Matschl, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 351 days.

(21) Appl. No.: 12/109,605

(22) Filed: Apr. 25, 2008

(65) Prior Publication Data

US 2008/0269594 A1    Oct. 30, 2008

Related U.S. Application Data

(60) Provisional application No. 60/914,403, filed on Apr. 27, 2007.

(51) Int. Cl.
*G01V 3/00* (2006.01)

(52) U.S. Cl. .................................. 324/307; 324/309

(58) Field of Classification Search ......... 324/300–322; 600/407–445; 250/363.03, 363.04
See application file for complete search history.

(56) References Cited

U.S. PATENT DOCUMENTS

| 7,368,912 B2* | 5/2008 | Kreibich ..................... 324/307 |
| 7,626,389 B2* | 12/2009 | Fiedler et al. ............... 324/309 |
| 2003/0194050 A1* | 10/2003 | Eberhard et al. .............. 378/37 |
| 2007/0102641 A1* | 5/2007 | Schmand et al. ....... 250/363.03 |
| 2010/0063516 A1* | 3/2010 | Parmer et al. ............... 606/130 |

* cited by examiner

*Primary Examiner*—Brij B Shrivastav
(74) *Attorney, Agent, or Firm*—Peter L. Kendall

(57) ABSTRACT

A phantom and method are provided for co-registering a magnetic resonance image and a nuclear medical image. The phantom includes a first housing defining a first chamber configured to receive a magnetic resonance material upon which magnetic resonance imaging can be performed in order to produce the magnetic resonance image. The phantom also includes three or more second housings configured to be attached to the first housing, where the second housings each define a second chamber configured to receive a radioactive material upon which nuclear imaging can be performed in order to produce the nuclear medical image and upon which the magnetic imaging can be performed in order to produce the magnetic resonance image. The first chamber has a volumetric capacity that is larger than a volumetric capacity of each second chamber.

20 Claims, 4 Drawing Sheets

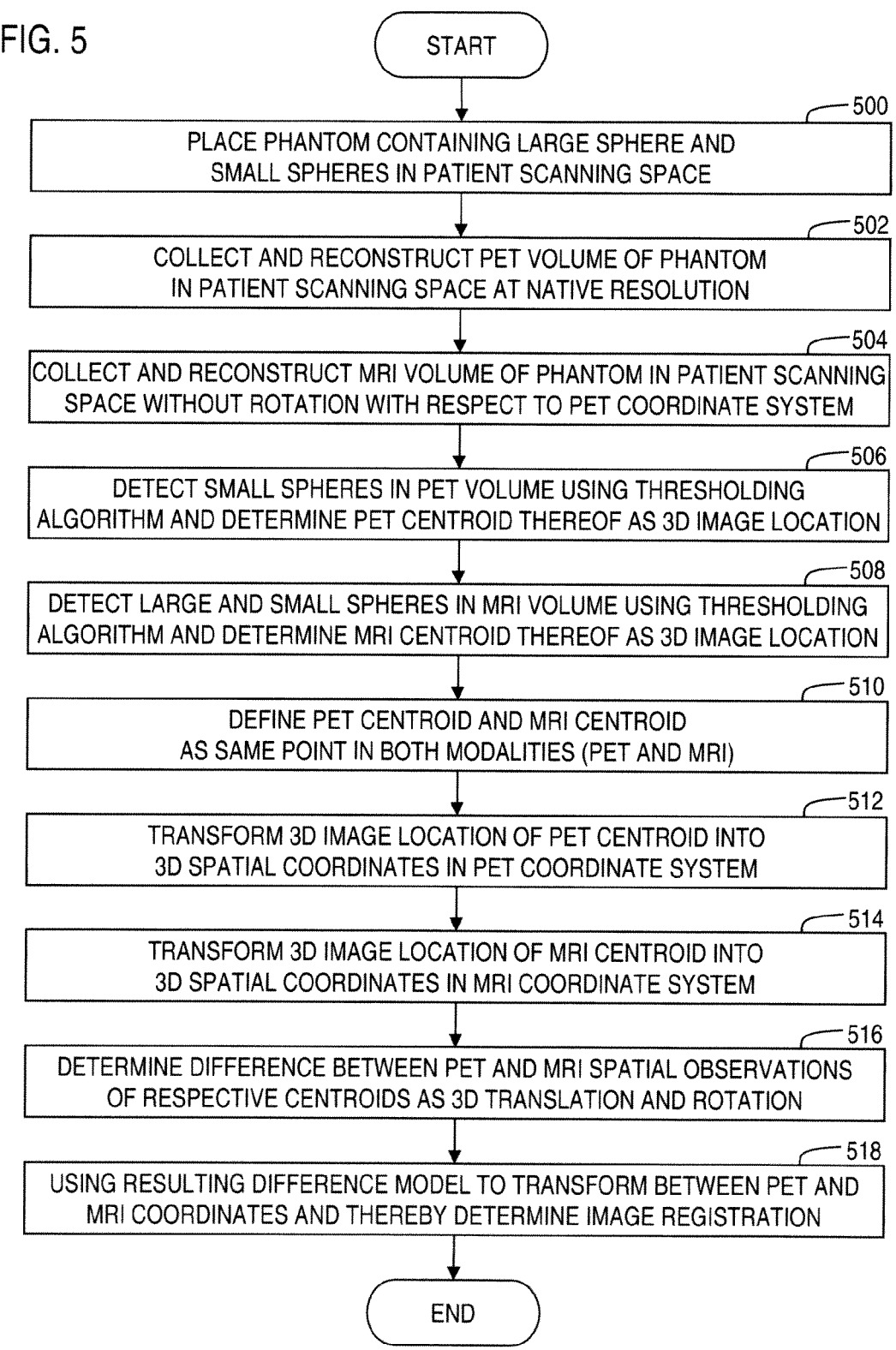

ered and aligned;
APPARATUS AND METHOD FOR IMAGE ALIGNMENT FOR COMBINED POSITRON EMISSION TOMOGRAPHY (PET) AND MAGNETIC RESONANCE IMAGING (MRI) SCANNER

PRIORITY CLAIM TO RELATED APPLICATION

This application claims priority from U.S. Provisional Patent Application Ser. No. 60/914,403, filed Apr. 27, 2007, the disclosure of which is incorporated by reference in its entirety herein.

FIELD

The present invention, according to certain embodiments, relates to combined nuclear medicine imaging, such as positron emission tomography (PET), and magnetic resonance imaging (MRI).

BACKGROUND

Magnetic resonance imaging (MRI) is primarily used in medical imaging to visualize anatomical structure of a patient's body. MRI technology can provide detailed images of the body in any plane. MRI has the ability to show soft tissue contrasts, which makes MRI scans especially useful in neurological, musculoskeletal, cardiovascular, and oncological imaging. MRI scans use a powerful magnetic field to align the magnetization of hydrogen atoms in the body. Radio waves are used to systematically alter the alignment of such magnetization, thereby causing the hydrogen atoms to produce a rotating magnetic field detectable by a scanning device of the MRI system. The resulting signal can be manipulated by additional magnetic fields to build up enough information to reconstruct an image of the body.

Positron emission tomography (PET) is a nuclear medicine imaging technique that produces a three-dimensional image or map of functional processes in a patient's body. A PET system detects pairs of gamma rays emitted indirectly by a positron-emitting radioisotope, which is introduced into the body on a metabolically active molecule. As the radioisotope undergoes positron emission decay (also known as positive beta decay), it emits a positron, the antimatter counterpart of an electron. After travelling up to a few millimeters, the positron encounters and annihilates with an electron, producing a pair of annihilation (gamma) photons moving in opposite directions, which are then detected when they reach a scintillator material in a scanning device of the PET system. Images of metabolic activity in space are then reconstructed by computer analysis.

The most significant fraction of electron-positron decays result in two 511 keV gamma photons being emitted at almost 180 degrees to each other. Thus, it is possible to localize the source of the positron annihilation event along a straight line of coincidence (also referred to as a line of response (LOR)), and then an image reconstruction can be performed using coincidence statistics. For example, using statistics collected from tens-of-thousands of coincidence events, a set of simultaneous equations for a total activity of each parcel or bit of tissue (also called a voxel) along many LORs can be solved by a number of techniques, and thus a map of radioactivities as a function of location for parcels or bits of tissue can be constructed and plotted. The resulting map shows the tissues in which the molecular probe has become concentrated, and the resulting map can be interpreted by a physician and used for patient diagnosis and treatment.

PET scans are increasingly read alongside CT scans or MRI scans, in an attempt to produce a combination image by "co-registration" that gives the physician both anatomic and metabolic information about the patient's body. It is widely accepted that co-registration of anatomical information improves the diagnostic value of functional imaging, as can be seen in the success of hybrid scanners using PET and CT imaging. But the combination of PET and MRI may also offer advantages, such as higher soft tissue contrast in the MRI anatomical images, real simultaneous acquisition, and minimum radiation exposure to the patient. However, numerous obstacles have been present that have limited the ability to fully integrate PET and MRI systems into a combined scanner that produces accurate co-registration of the PET and MRI images.

Thus, there is a clear need for an improved method and apparatus for providing image alignment for combined positron emission tomography (PET) and magnetic resonance imaging (MRI) scanning.

DISCLOSURE

The present disclosure advantageously provides a phantom that can be used, for example, for co-registering a magnetic resonance image and a nuclear medical image, where an embodiment of the phantom includes a first housing defining a first chamber configured to receive a magnetic resonance material upon which magnetic resonance imaging can be performed in order to produce the magnetic resonance image, and three or more second housings configured to be attached to the first housing, wherein the second housings each define a second chamber configured to receive a radioactive material upon which nuclear imaging can be performed in order to produce the nuclear medical image and upon which the magnetic imaging can be performed in order to produce the magnetic resonance image. The first chamber has a volumetric capacity that is larger than a volumetric capacity of each second chamber.

The present disclosure also advantageously provides a method that can be used, for example, for co-registering a magnetic resonance image and a nuclear medical image, where the method includes placing a phantom in a patient scanning space, where the phantom includes a first housing defining a first chamber containing a magnetic resonance material, and three or more second housings attached to the first housing, where the second housings each define a second chamber containing a radioactive material, and where the first chamber has a volumetric capacity that is larger than a volumetric capacity of each second chamber. The method also includes performing a magnetic resonance imaging scan and nuclear imaging scan on the phantom in the patient scanning space to collect a magnetic resonance imaging volume and a nuclear medical imaging volume, and determining co-registration of the magnetic resonance image and the nuclear medical image using the magnetic resonance imaging volume and the nuclear medical imaging volume.

BRIEF DESCRIPTION OF THE DRAWINGS

Various exemplary embodiments are illustrated by way of example, and not by way of limitation, in the figures of the accompanying drawings in which like reference numerals refer to similar elements and in which:

FIG. 5 is a flow chart setting forth a process for providing image alignment for combined PET and MRI scanning, according to an exemplary embodiment.

DESCRIPTION OF THE PREFERRED EMBODIMENTS

A method and apparatus for providing image alignment for combined positron emission tomography (PET) and magnetic resonance imaging (MRI) are described. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Co-registration of anatomical information can greatly improve the diagnostic value of functional imaging. For example, the combination of PET and MRI images can offer numerous advantages, such as higher soft tissue contrast in the MRI anatomical images, real simultaneous acquisition, and minimum radiation exposure to the patient. Correlative imaging can open exciting new applications in oncology, neurology, and cardiology. Combining functional information from nuclear medical imaging with anatomical information from CT or MRI images has become of great interest since PET tracers are becoming more and more specific. Image co-registration and fusion techniques are been developed and optimized for the interpretation of PET, CT, and MRI data. While medical imaging apparatuses that combine PET and CT systems in one hardware device have been used in oncology, the combination of PET with MRI exhibits several technical challenges.

Figure 1:
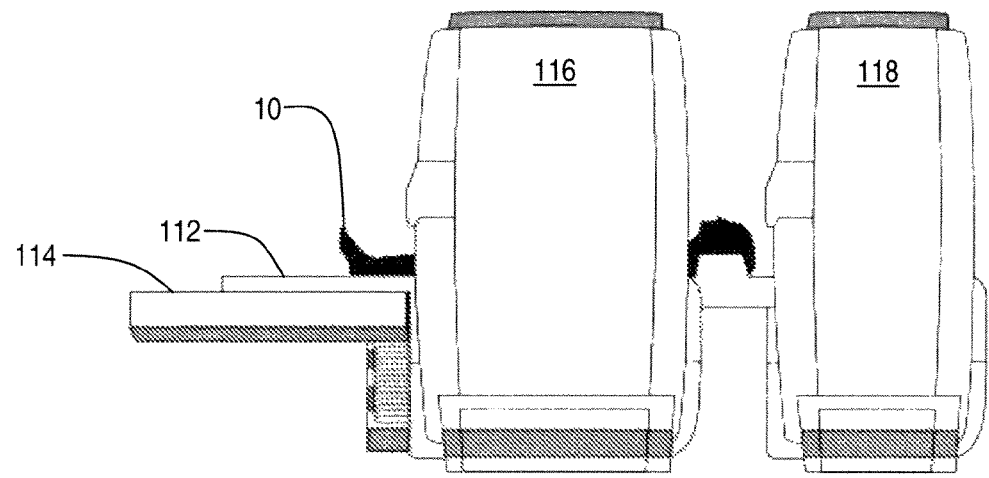
FIG. 1 is a combined positron emission tomography (PET) and magnetic resonance imaging (MRI) scanning system in which the PET scanner and the MRI scanner are axially offset and aligned.

FIG. 1 depicts one possible PET-MRI scanner system. In the PET-MRI scanner system shown in FIG. 1, a patient 10 is positioned on a pallet 112 that is movably supported by a table 114. The pallet 112 is axially movable on the table 114 in a left-right direction as shown in FIG. 1. The PET-MRI scanner system in FIG. 1 includes an MRI scanner 116 and a PET scanner 118 that are axially aligned along the moving direction of the pallet. Thus, the patient 10 can be moved through a patient scanning space in the MRI scanner 116 and through a patient scanning space in the PET scanner 118 to perform sequential imaging in each scanner. However, such sequential imaging can prove to be troublesome, since generating a combination image by co-registration of the PET image and the MRI image can be very difficult and inaccurate. For example, when PET and MRI datasets are acquired separately, as in such a sequential imaging arrangement, alignment inaccuracies can frequently occur between the PET image and the MRI image due, for example, to movement or repositioning of patient during scanning.

Figure 2:
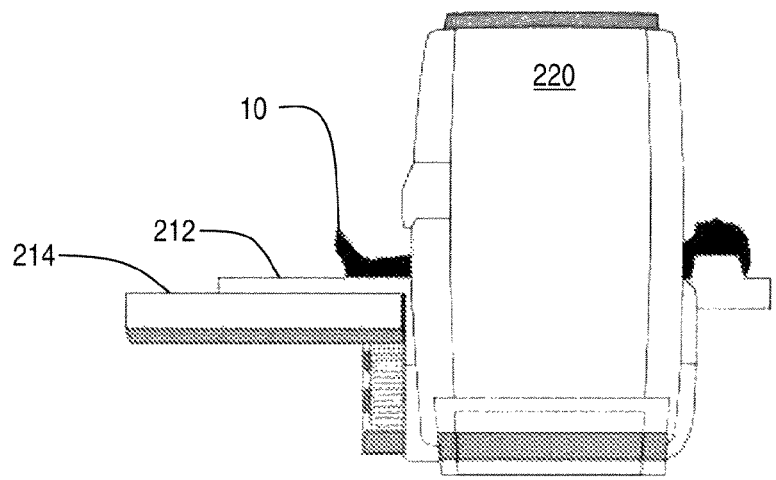
FIG. 2 is a combined PET and MRI scanning system in which the PET scanner and the MRI scanner are provided in a single unit for simultaneous PET and MRI scanning, according to an exemplary embodiment.

In order to reduce such alignment inaccuracies, another possible PET-MRI scanner system can be provided that performs simultaneous PET and MRI scans. FIG. 2 depicts an embodiment of such a combined PET-MRI scanner system with simultaneous measurements. In the embodiment of FIG. 2, the patient 10 is positioned on a pallet 212 that is movably supported by a table 214. The pallet 212 is axially movable on the table 214 in a left-right direction as shown in FIG. 2. The PET-MRI scanner system in FIG. 2 includes a combined PET and MRI scanner 220 that houses both an MRI scanner and a PET scanner that can simultaneously scan the patient 10 as the patient 10 is axially moved through a patient scanning space in the combined PET and MRI scanner 220. As the PET imaging and the MRI imaging are performed simultaneously along the patient's body, the alignment inaccuracies noted above can be reduced or eliminated.

In principle, a combined PET and MRI scanner will provide simultaneous functional and anatomical information with near perfect spatial registration. By fully integrating a PET scanner inside a magnet of an MRI scanner, true simultaneous imaging be realized. However, both PET and MRI images are based on different coordinate systems (image domains), which can not be readily aligned as in the case of PET-CT image modality. The PET image domain (x, y, z) coordinate system is fixed in "absolute" space and it is relative to the PET gantry with in the scanner. Thus, the positioning of the PET coordinate system is known through engineering design. On the other hand, the MRI image domain ($x_m$, $y_m$, $z_m$) coordinate system is not absolute in space and will change based on several MRI specific tuning and shimming procedures, thereby making the alignment of both modalities difficult. Accordingly, a special alignment procedure is needed in order to achieve a valid image fusion (co-registration) of both a PET imaging modality and an MRI modality.

Figure 3:
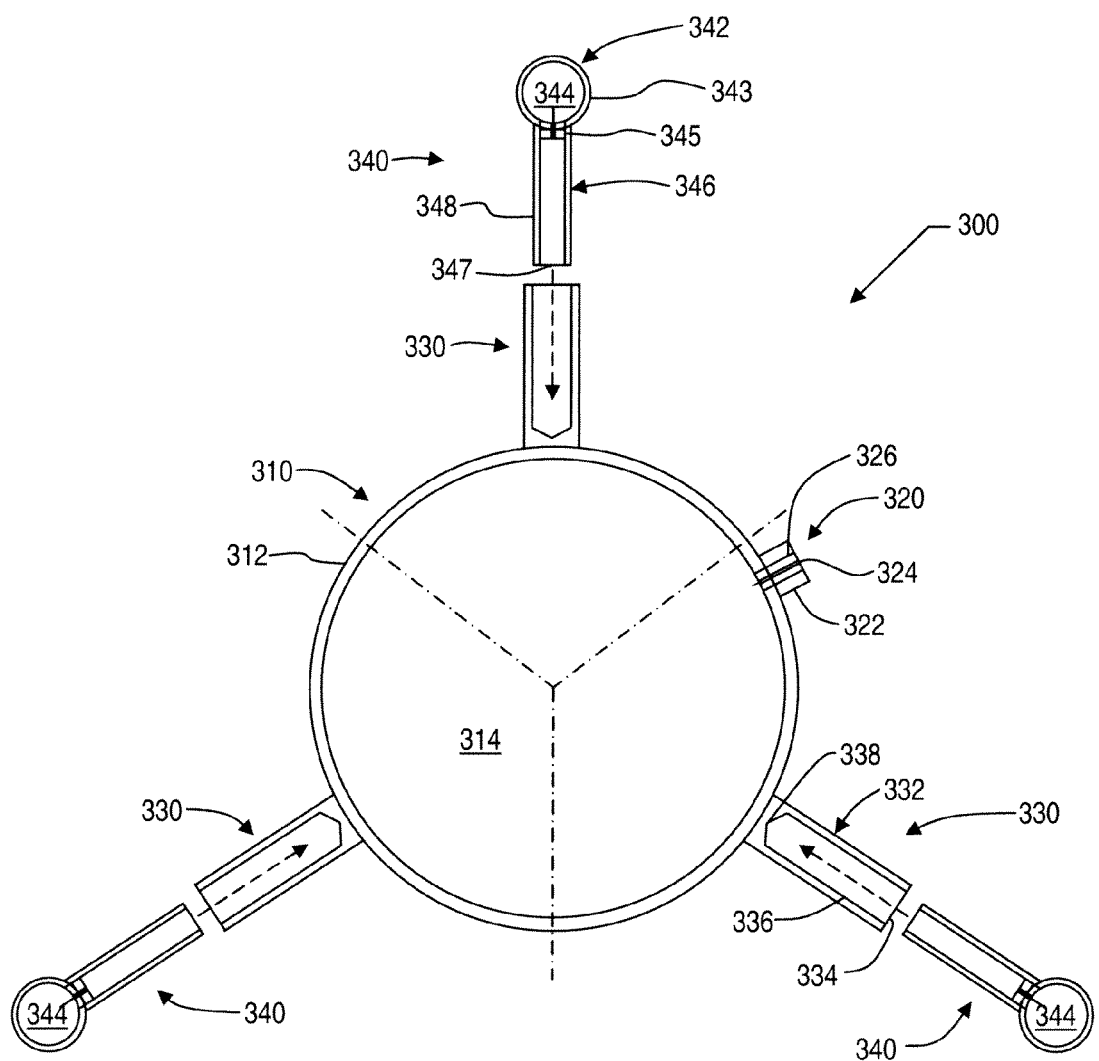
FIG. 3 is a cross-sectional view of a PET-MRI phantom for use in a process for providing image alignment for combined PET and MRI scanning, according to an exemplary embodiment.
Figure 4:
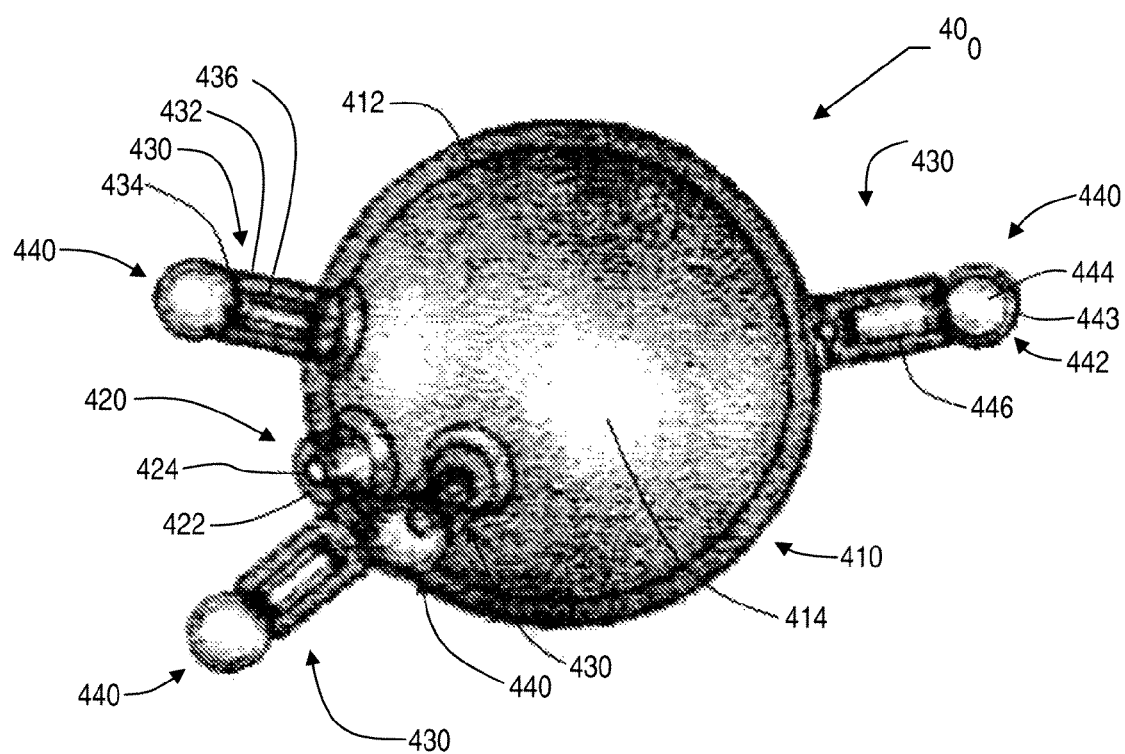
FIG. 4 is a perspective view of a PET-MRI phantom for use in a process for providing image alignment for combined PET and MRI scanning, according to another exemplary embodiment.

FIGS. 3 and 4 depict embodiments of PET-MRI phantoms that can be used with an alignment procedure to align PET and MRI modalities in order to provide image registration, according to embodiments of the present invention. Such PET-MRI phantoms can be used with a fully automated alignment algorithm to provide an advantageous alignment procedure. Embodiments of the PET-MRI phantom meet requirements regarding visibility for both the PET scanning system and the MRI scanning system, in order to provide a dual-system phantom.

In the embodiment shown in FIG. 3, a PET-MRI phantom 300 is depicted that includes a large sphere 310 at a center of the phantom, and three small sphere units 340 each having a small sphere 342, which are dispersed around the large sphere 310. (Note that FIG. 3 depicts the small sphere units 340 in exploded view as detached from the remainder of the phantom 300; however, during use of the phantom, the small sphere units 340 would be attached to the phantom as shown by the dashed-line arrows. Also, note that the phantom 300 is shown as having three quadrants defined by the dash-dot lines extending from the center; however, these quadrants are imaginary and are merely shown in order to depict the three small sphere units in a same plane for illustrative purposes, while in fact the small sphere units may not be provided in the same plane, as will be discussed in greater detail below.)

The large sphere 310 at the center of the PET-MRI phantom 300 includes a hollow spherical housing 312. The hollow spherical housing 312 defines a chamber 314 that is used to retain a fluid material (or magnetic resonance material) upon which the MRI scan acts to generate an MRI image. The chamber 314 can contain a NaCl solution dissolved in water as the fluid material, such that the salt therein represents a certain load for MRI transmit and receive coils of the MRI scanning device, and such that hydrogen inside the water compound delivers an MRI signal at a certain resonance frequency, which can be detected by the MR receive coil. However, alternatively, the chamber 314 is preferably filled with silicones containing hydrogen as the fluid material. The chamber 314 preferably has a volumetric capacity of 200 ml, thus being capable of receiving 200 ml of the silicones containing hydrogen. The 200 ml of silicones containing hydrogen provide the MRI scanning system with enough mass of hydrogen to allow for frequency and transmitter adjustment. During scanning, the large sphere 310 containing the fluid material is generally only visible in the MRI scan, and not in the PET scan.

The large sphere 310 of the PET-MRI phantom 300 also includes a port 320 that allows for the fluid material to be injected into or extracted out of the chamber 314. The port 320 includes a tubular body 322 having an opening 324 extending therethrough and being in fluid connection with the chamber 314. The port 320 also includes a valve 326 that regulates the flow of fluid into and out of the chamber 314.

The housing 312 of the large sphere 310 also includes mounting structures 330 on an outer surface of thereof that are used to mount the small sphere units 340 to the phantom 300 in order to provide a unitary structure of the phantom during use thereof. The mounting structures 330 include a tubular portion 332 having a first end with an opening 334 to receive a small sphere unit therein, and an opposite closed end 338. The inner surface 336 of the tubular portion 332 preferably contains an engagement structure used to engage the small sphere unit to the mounting structure. For example, the inner surface 336 can include a threaded structure (i.e., a tapped thread on the inner surface 336) as the engagement structure. However, other engagement structures could be used that reliably join the small sphere unit to the mounting structure, and allow for selective engagement and disengagement therebetween as desired.

At least three small spheres 342 surround the large sphere 310. In this embodiment, each small sphere 342 is provided as part of a small sphere unit 340. The small sphere 342 includes a hollow spherical housing 343. The hollow spherical housing 343 defines a chamber 344 that is used to retain a fluid material upon which the PET scan acts to generate a PET image. The chamber 344 contains a radioactive material that emits 511 keV gamma-rays in coincidence, as the fluid material. For example, the chamber 344 can contain $^{68}$Germanium or $^{18}$FDG. Such coincidences can be detected by the PET scanning system, and then the image can be reconstructed from such coincidences.

However, in this embodiment, the chamber 344 is preferably filled with a radioactive silicon germanium mixture that makes the small spheres 342 visible to both the PET scanning system and the MRI scanning system. The chamber 344 preferably has a volumetric capacity of 0.5 ml, thus being capable of receiving 0.5 ml of the radioactive material. This configuration allows the small spheres to be as small as possible, yet still be seen in both PET and MRI modalities. The radioactive material contained within each of the small spheres 342 preferably holds an activity of about 0.3 mCi. This amount of activity, in combination with the volume of the small spheres, produces a sharp hot spot in the PET image, which can be used for co-registration with the MRI image. Silicon was chosen as a carrier for the radioactivity because it has good visibility in the MRI when special acquisition techniques are used with short echo times. Silicon is also mixable with activity and prevents leakage of activity in the assembled phantom.

The small sphere units 340 each also include a rod portion 346 with the small sphere 342 being attached to one end of the rod portion 346. The rod portion 346 is generally hollow and has an opening 347 at an end opposite to the end thereof attached to the small sphere 342. The opening 347 extends through the rod portion 346 and is in fluid connection with the chamber 344. A valve 345 is provided within the rod portion 346 that regulates the flow of fluid into and out of the chamber 344. The outer surface 348 of the rod portion 346 preferably contains an engagement structure used to engage the small sphere unit to the mounting structure. For example, the outer surface 348 can include a threaded structure (i.e., a die thread on the outer surface 348) that engages to the engagement structure on the inner surface 336 of the mounting structure 330.

In order to increase the serviceability of the PET-MRI alignment phantom 300, the small sphere units 340 are attached via a threaded engagement, thereby making them replaceable. So when the activity of the small spheres 342 decay too much, the small sphere units 340 containing the small spheres 342 can be replaced without swapping the whole phantom. This configuration also makes it easier to ship the phantom, since the radioactive material and the phantom can be stored separately, and the radioactive material can be injected into the phantom at the site, thereby circumventing international shipping requirements for radioactive materials.

The phantom contains at least three small spheres positioned in all three dimensions such as an unambiguous transformer (3 translations, 3 rotations) could be found. While the embodiment shown in FIG. 3 has three small spheres 342, the phantom can be provided with more than three small spheres. For example, FIG. 4 depicts an embodiment that contains more than three small spheres, and such redundancy can make the alignment process more reliable.

In the embodiment shown in FIG. 4, a PET-MRI phantom 400 is depicted that includes a large sphere 410 at a center of the phantom, and four small sphere units 440 each having a small sphere 442, which are dispersed around the large sphere 410. (Note that FIG. 4 depicts the small sphere units 440 as being attached to the phantom, which is the configuration in which the phantom is used.)

The large sphere 410 at the center of the PET-MRI phantom 400 includes a hollow spherical housing 412. The hollow spherical housing 412 defines a chamber 414 that is used to retain a fluid material upon which the MRI scan acts to generate an MRI image. The chamber 414 is preferably filled with silicones containing hydrogen as the fluid material. The chamber 414 preferably has a volumetric capacity of 200 ml, thus being capable of receiving 200 ml of the silicones containing hydrogen. The large sphere 410 of the PET-MRI phantom 400 also includes a port 420 that allows for the fluid material to be injected into or extracted out of the chamber 414. The port 420 includes a tubular body 422 having an opening 424 extending therethrough and being in fluid connection with the chamber 414. The port 420 also includes a valve that regulates the flow of fluid into and out of the chamber 414.

The housing 412 of the large sphere 410 also includes mounting structures 430 on an outer surface of thereof that are used to mount the small sphere units 440 to the phantom 400 in order to provide a unitary structure of the phantom during use thereof. The mounting structures 430 include a tubular portion 432 having a first end with an opening 434 to receive a small sphere unit therein, and an opposite closed end. The inner surface 436 of the tubular portion 432 preferably contains an engagement structure used to engage the small sphere unit to the mounting structure. For example, the inner surface 436 can include a threaded structure (i.e., a tapped thread on the inner surface 436) as the engagement structure. However, other engagement structures could be used that reliably join the small sphere unit to the mounting structure, and allow for selective engagement and disengagement therebetween as desired.

In this embodiment, four small spheres 442 surround the large sphere 410. Each small sphere 442 is provided as part of a small sphere unit 440. The small sphere 442 includes a hollow spherical housing 443. The hollow spherical housing 443 defines a chamber 444 that is used to retain a fluid material upon which the PET scan acts to generate a PET image. The chamber 444 contains a radioactive material that emits 511 keV gamma-rays in coincidence, as the fluid material. For example, the chamber 444 is preferably filled with a radioactive silicon germanium mixture that makes the small spheres 442 visible to both the PET scanning system and the MRI scanning system. The chamber 444 preferably has a volumetric capacity of 0.5 ml, thus being capable of receiving 0.5 ml of the radioactive material. The radioactive material contained within each of the small spheres 442 preferably holds an activity of about 0.3 mCi.

The small sphere units 440 each also include a rod portion 446 with the small sphere 442 being attached to one end of the rod portion 446. The rod portion 446 is generally hollow and has an opening at an end opposite to the end thereof attached to the small sphere 442. The opening extends through the rod portion 446 and is in fluid connection with the chamber 444. A valve is provided within the rod portion 446 that regulates the flow of fluid into and out of the chamber 444. The outer surface of the rod portion 446 preferably contains an engagement structure used to engage the small sphere unit to the mounting structure. For example, the outer surface can include a threaded structure (i.e., a die thread on the outer surface) that engages to the engagement structure on the inner surface 436 of the mounting structure 430.

FIG. 5 depicts a process for aligning PET and MRI images. In step 500, the process begins by placing a phantom (e.g., phantom 300 in FIG. 3, or phantom 400 in FIG. 4) in a patient scanning space of a combined PET and MRI scanner (e.g., as depicted in FIG. 2). For example, the phantom can be fixedly mounted to the patient pallet. The phantom contains a large sphere containing a fluid material upon which the MRI scan acts to generate an MRI image, and three or more small spheres containing a fluid material containing radioactive material upon which the PET scan acts to generate a PET image.

The co-registration of the PET and MRI images is performed with a rigid transformation. The co-registration is relatively easy due to the spatial orientation of the elements composing the phantom. The phantom contains at least three small spheres positioned in all three dimensions, so as to provide an unambiguous transformation (three translations, three rotations). Note that the three scaling are fixed, since pixel sizes are known for both modalities. As noted above, more than three spheres can be utilized, and such redundancy can make the alignment process more reliable.

The alignment process proceeds in steps 502 and 504 by collecting a PET volume and an MRI volume in the space planned for patient scans. Thus, in step 502, the PET volume of the phantom in the patient scanning space is collected and reconstructed at its native (highest) resolution. The particular configuration selected for the small spheres avoids the need for attenuation and scatter corrections, although those corrections could be estimated using an attenuation template derived either from CT or MRI. And, in step 504, the MRI volume of the phantom in the patient scanning space is collected and reconstructed without rotation with respect to the PET coordinate system. The MRI volume is acquired with 1 mm isotropic voxels and without rotation with respect to the PET coordinate system. Note that the two gantries can have a small relative rotation due to mechanical tolerance even when the PET is an insert, e.g., in the case of FIG. 2 (note that implicitly a transformer is expected for the configuration shown in FIG. 1).

In step 506, the small spheres are detected in the PET volume using a thresholding algorithm, and a PET centroid thereof is determined as a 3D image location. Also, in step 508, the large and small spheres are detected in the MRI volume using a thresholding algorithm, and an MRI centroid thereof is determined as a 3D image location. Thus, with a simple thresholding algorithm, the spheres can be detected in each of the PET and MRI volumes. The centroid of these spheres is taken as conjugate observations of the same point in each modality. Thus, in step 510, the PET centroid and the MRI centroid are defined as the same point in both modalities. Then, in steps 512 and 514, these 3D image locations are transformed into 3D spatial coordinates. More specifically, the 3D image location of the PET centroid is transformed into 3D spatial coordinates in the PET coordinate system in step 512, and the 3D image location of the MRI centroid is transformed into 3D spatial coordinates in the MRI coordinate system in step 514.

In step 516, a difference between the PET and MRI spatial observations of the respective centroids is determined as a 3D translation and rotation. The difference in the PET and MRI spatial observations is modeled as a 3D translation and rotation and the best fit is solved with a least squares equation. The resulting model allows the transformation between PET and MRI coordinates, and image registration. Accordingly, in step 518, the resulting difference model is used to transform between PET and MRI coordinates and thereby determine image registration. Thus, a method and apparatus for providing image alignment for combined positron emission tomography (PET) and magnetic resonance imaging (MRI) scanning are set forth.

It should be noted that the exemplary embodiments depicted and described herein set forth the preferred embodiments of the present invention, and are not meant to limit the scope of the claims hereto in any way. Numerous modifications and variations of the present invention are possible in light of the above teachings. It is therefore to be understood that, within the scope of the appended claims, the invention may be practiced otherwise than as specifically described herein.

What is claimed is:

1. A phantom for co-registering a magnetic resonance image and a nuclear medical image, said phantom comprising:
   a first housing defining a first chamber configured to receive a magnetic resonance material upon which magnetic resonance imaging can be performed in order to produce the magnetic resonance image; and
   three or more second housings configured to be attached to said first housing, wherein said second housings each define a second chamber configured to receive a radioactive material upon which nuclear imaging can be performed in order to produce the nuclear medical image and upon which the magnetic imaging can be performed in order to produce the magnetic resonance image,
   wherein said first chamber has a volumetric capacity that is larger than a volumetric capacity of each second chamber.

2. The phantom according to claim 1, wherein:
   said first housing has a first centroid;
   said second housings each define a respective second centroid; and
   said second housings are each configured to be attached to said first housing such that each second centroid is located at a same distance from said first centroid.

3. The phantom according to claim 2, wherein said second housings are each configured to be attached to said first housing such that each second centroid is located along a separate three-dimensional axis centered at said first centroid.

4. The phantom according to claim 1, wherein:
   said first housing is spherical; and
   said second housings are each spherical.

5. The phantom according to claim 1, wherein:
said first chamber contains at least 200 ml of a silicone containing hydrogen as the magnetic resonance material; and
each second housing contains at least 0.5 ml of a radioactive silicon germanium mixture as the radioactive material.

6. The phantom according to claim 5, wherein said radioactive silicon germanium mixture in each second chamber has a specific activity of at least 0.3 mCi.

7. The phantom according to claim 1, wherein each second housing is detachably attached to said first housing.

8. The phantom according to claim 7, wherein:
each second housing is mounted to a rod portion;
said first housing has three or more tubular portions, said tubular portions each being configured to receive a respective rod portion of each second housing; and
said tubular portions and respective rod portions being configured to threadedly engage with each other.

9. The phantom according to claim 1, wherein:
said first housing has a first opening with a first valve that is configured to regulate a flow of the magnetic resonance material into and out of said first chamber; and
said second housings each have a second opening with a second valve that is configured to regulate a flow of the radioactive material into and out of a respective second chamber.

10. A method of co-registering a magnetic resonance image and a nuclear medical image, said method comprising:
placing a phantom in a patient scanning space, the phantom including a first housing defining a first chamber containing a magnetic resonance material, and three or more second housings attached to the first housing, wherein the second housings each define a second chamber containing a radioactive material, and wherein the first chamber has a volumetric capacity that is larger than a volumetric capacity of each second chamber;
performing a magnetic resonance imaging scan and nuclear imaging scan on the phantom in the patient scanning space to collect a magnetic resonance imaging volume and a nuclear medical imaging volume; and
determining co-registration of the magnetic resonance image and the nuclear medical image using the magnetic resonance imaging volume and the nuclear medical imaging volume.

11. The method according to claim 10, wherein the magnetic resonance imaging scan and the nuclear imaging scan performed on the phantom in the patient scanning space are performed simultaneously.

12. The method according to claim 11, wherein:
the nuclear medical imaging volume is collected and reconstructed at a native resolution; and
the magnetic resonance imaging volume is collected and reconstructed without rotation with respect to a coordinate system of the nuclear medical imaging volume.

13. The method according to claim 12, further comprising:
detecting a threshold amount of the radioactive material in each second chamber in the nuclear medical imaging volume;
determining a nuclear medical imaging centroid defined as a centroid of the detection in the nuclear medical imaging volume;
detecting a threshold amount of the magnetic resonance material in the first chamber and the radioactive material in each second chamber in the magnetic resonance imaging volume; and
determining a magnetic resonance imaging centroid defined as a centroid of the detection in the magnetic resonance imaging volume.

14. The method according to claim 13, further comprising:
defining the nuclear medical imaging centroid and the magnetic resonance imaging centroid as a common point in both the nuclear medical imaging volume and the magnetic resonance imaging volume.

15. The method according to claim 14, further comprising:
transforming an image location of the nuclear medical imaging centroid into a nuclear medical imaging three-dimensional spatial coordinate system;
transforming an image location of the magnetic resonance imaging centroid into a magnetic resonance imaging three-dimensional spatial coordinate system; and
forming a difference model by determining spatial differences between the image location of the nuclear medical imaging centroid and the image location of the magnetic resonance imaging centroid as three-dimensional rotations and/or translations using the common point as a reference.

16. The method according to claim 15, wherein the co-registration of the magnetic resonance image and the nuclear medical image is determined using the difference model.

17. The method according to claim 10, wherein:
the first housing is spherical and has a first centroid;
the second housings are each spherical and each define a respective second centroid;
the second housings are each configured to be attached to the first housing such that each second centroid is located at a same distance from the first centroid; and
the second housings are each configured to be attached to the first housing such that each second centroid is located along a separate three-dimensional axis centered at the first centroid.

18. The method according to claim 17, wherein:
the first chamber contains at least 200 ml of a silicone containing hydrogen as the magnetic resonance material;
each second housing contains at least 0.5 ml of a radioactive silicon germanium mixture as the radioactive material; and
the radioactive silicon germanium mixture in each second chamber has a specific activity of at least 0.3 mCi.

19. The method according to claim 10, wherein:
each second housing is detachably attached to the first housing;
each second housing is mounted to a rod portion;
the first housing has three or more tubular portions, the tubular portions each being configured to receive a respective rod portion of each second housing; and
the tubular portions and respective rod portions being configured to threadedly engage with each other.

20. The method according to claim 10, wherein:
the first housing has a first opening with a first valve that is configured to regulate a flow of the magnetic resonance material into and out of the first chamber; and
the second housings each have a second opening with a second valve that is configured to regulate a flow of the radioactive material into and out of a respective second chamber.

* * * * *